United States Patent [19]

Mackles et al.

[11] Patent Number: 4,889,709

[45] Date of Patent: * Dec. 26, 1989

[54] AEROSOL FOAM WITH ADSORBATE AND CONTAINER CONTAINING SAME

[75] Inventors: Leonard Mackles, New York, N.Y.; Leonard Chavkin, Bloomsbury, N.J.

[73] Assignee: Product Resources International, Inc., New York, N.Y.

[*] Notice: The portion of the term of this patent subsequent to Jun. 21, 2005 has been disclaimed.

[21] Appl. No.: 208,254

[22] Filed: Jun. 17, 1988

Related U.S. Application Data

[63] Continuation-in-part of Ser. No. 5,597, Jan. 21, 1987, Pat. No. 4,752,465, which is a continuation-in-part of Ser. No. 778,026, Sep. 20, 1985, Pat. No. 4,639,367, which is a continuation-in-part of Ser. No. 713,294, Mar. 18, 1985, abandoned.

[51] Int. Cl.$^4$ .......................... A61K 9/00; A61L 9/04
[52] U.S. Cl. ...................................... 424/45; 514/945; 252/305
[58] Field of Search ..................... 424/45; 514/945; 252/305

[56] References Cited

U.S. PATENT DOCUMENTS

| | | | |
|---|---|---|---|
| 3,135,658 | 6/1964 | Hanus et al. | 424/45 |
| 3,337,402 | 8/1967 | Zentner | 424/45 |
| 3,419,658 | 12/1968 | Sanders | 424/45 |
| 3,770,648 | 11/1973 | Mackles | 424/45 |
| 3,849,580 | 11/1974 | Sejpal | 424/45 |
| 3,929,985 | 12/1975 | Webb, Jr. | 424/45 |
| 4,174,295 | 11/1979 | Bargigia et al. | 424/45 |
| 4,188,412 | 2/1980 | Sejpal | 426/609 |
| 4,224,319 | 9/1980 | Marcadet | 424/238 |
| 4,425,164 | 1/1984 | Bliznak | 106/150 |
| 4,639,367 | 1/1987 | Mackles | 424/45 |
| 4,752,465 | 6/1988 | Mackles | 514/945 |
| 4,780,309 | 10/1988 | Gena et al. | 514/945 |

FOREIGN PATENT DOCUMENTS 933486 8/1963 United Kingdom .
1121358 7/1968 United Kingdom .

OTHER PUBLICATIONS

Veegum Brochure.

*Primary Examiner*—Harold D. Anderson
*Assistant Examiner*—Nathan M. Nutter
*Attorney, Agent, or Firm*—Amster, Rothstein & Ebenstein

[57] ABSTRACT

A stable, edible anhydrous aerosol foam comprises a foamable liquid oil, a foaming agent, a food grade propellant, and at least 15 wt % dispersed solid particles including an adsorbate of an active therapeutic agent on magnesium aluminum silicate. The foam is a stable whip having the consistency of whipped cream and can be dispensed in repeatable and measurable quantities onto a spoon. It is useful to dispense a wide variety of active, therapeutic agents and, in particular, as an alternative to tablets or capsules which are hard to swallow or liquid medicines having a bad taste.

23 Claims, No Drawings

AEROSOL FOAM WITH ADSORBATE AND CONTAINER CONTAINING SAME

RELATED APPLICATIONS

This application is a continuation-in-part of U.S. patent application Ser. No. 005,597, filed Jan. 21, 1987, now U.S. Pat. No. 4,752,465, issued June 21, 1988, which is in turn a continuation-in-part of U.S. patent application Ser. No. 778,026, filed Sept. 20, 1985, now U.S. Pat. No. 4,639,367, issued Jan. 27, 1987, which is in turn a continuation-in-part of U.S. patent application Ser. No. 713,294, filed Mar. 18, 1985, now abandoned.

BACKGROUND OF THE INVENTION

Tablets and capsules are the most common dosage forms for the oral administration of nutritional, medicinal, or other therapeutic products. It is well known, however, that these dosage forms are unacceptable for use by people who have difficulty in swallowing tablets and capsules and that the difficulty is exacerbated by larger tablets and capsules and, in some instances, by the bad taste of the medication. It is generally accepted that these types of problems with medications are serious because they may lead to a failure on the part of patients to comply with the medication regimen ordered by the physician.

The common alternatives to conventional tablets and capsules are chewable tablets and aqueous or hydroalcoholic liquids such as syrups, suspensions and elixirs. Such dosage forms are commonly used for analgesics, cough and cold medications, antibiotics, vitamins and many other nutritional or medicinal products. In general, these forms do not significantly improve the taste of a medication or make it easier to swallow larger doses.

Normally, therapeutic amines such as dextromethorphan, phenylpropanolamine, pseudoephedrine, chlorpheniramine, triprolidine, among others, are very bitter when used in therapeutic concentrations. Efforts to overcome or mask this bitterness have not been completely successful. An adsorbate marketed for this purpose is composed of dextromethorphan hydrobromide (10%) adsorbed on a substrate (90%) of magnesium trisilicate. When this adsorbate is used in therapeutic concentrations, the bitterness of DMHBr is significantly reduced, but it is still present. Other materials have been recommended for use as adsorption substrates: e.g., clays such as magnesium aluminum silicate (available under the trade name Veegum) and hydrous aluminum silicate (bentonite). Clathrates (such as cyclodextrins), sodium aluminum silicates (zeolites) and ion-exchange resins have all been mentioned for this use—i.e., to form adsorbates that will mask bitter tastes.

The formation of adsorbates is believed to be an adsorption process, an ion-exchange process, or both. Heretofore, it was believed that adsorbates using a clay substrate would only form in aqueous systems on the grounds that the clay must hydrate and swell before its adsorptive properties develop. It has never been suggested that such adsorbates could be formed in non-aqueous oil systems.

In general these substrates for taste masking are rather difficult to use successfully. The active-substrate complex must typically be prepared separately (as in the case of the dextromethorphan hydrobromide/magnesium trisilicate adsorbate) and then added "preformed" to the pharmaceutical dosage form—e.g., a chewable tablet or lozenge. Thus, the standard procedure for forming an adsorbate is to hydrate the adsorption substrate (e.g., a clay such as magnesium aluminum silicate) in hot water (60° C.). The weight of the substrate is usually in the ratio of 10:1 to the drug. The drug, usually a HCl or HBr salt of an amine active therapeutic agent, is dissolved in sufficient hot water. The drug solution is added to the substrate suspension with high speed agitation. The entire mass will coagulate. The mass is then filtered, washed, dried and then pulverized to a fine powder. Drugs such as dextromethorphan HBr, pseudoephedrine HCl and phenylpropanolamine HCl can be adsorbed onto clays by this method, but the arduous nature of the procedure restricts its use.

Applicants' U.S. Pat. Nos. 4,639,367 and 4,752,465 describe stable, edible anhydrous aerosol foams comprising a foamable liquid oil, a foaming agent, a propellant and dispersed solid particles which may include active therapeutic agents. The foam is a stable whip having the consistency of whipped cream and can be dispensed in repeatable and measurable quantities onto a spoon. It is useful to dispense a wide variety of active therapeutic agents and serves as an alternative to tablets or capsules which are hard to swallow or liquid medicines having a bad taste. The substance of these patents is hereby incorporated by reference.

While the aerosol foams taught by these patents do not generally contain adsorbates, they are fully satisfactory for the masking of objectionable taste in most drugs, especially at low and medium therapeutic concentrations. However the extremely bitter taste of particular active therapeutic agents cannot be totally overcome or masked by this technique alone, especially when the agents are used at particularly high levels. The patents illustrate the use of an adsorbate to assist in overcoming such bitter tastes. Thus, Example 17 of U.S. Pat. No. 4,639,367 discloses the use of magnesium aluminum silicate in connection with the formation of a foam whip of trimethoprim (a urinary tract drug). Nonetheless, there remain particular amine active therapeutic agents of such extreme bitterness that, when employed at high concentrations, their bitter taste cannot be overcome, even by an aerosol foam in which the amine form of the drug is adsorbed on magnesium aluminum silicate as taught by these examples.

Accordingly, an object of the present invention is to provide a stable, edible anhydrous aerosol foam or whip which can mask the bitter taste of an amine active therapeutic agent, even at a high therapeutic concentration.

Another object is to provide such an aerosol foam which employs adsorbate technology without requiring pre-formation of the adsorbate.

A further object is to provide such an aerosol foam which may be easily and rapidly formed, creating a taste-masking adsorbate in situ.

SUMMARY OF THE DISCLOSURE

It has now been found that the above and related objects are obtained in a stable, edible, anhydrous aerosol foam or whip capable of suspending up to 50% by weight of dispersed solids comprising a foamable, edible anhydrous liquid oil; a foaming agent; controlled amounts of a food grade propellant which are sufficient to produce a stable foam rather than a spray; and at least 15% by weight of dispersed solids including an active therapeutic agent. The aerosol foam or whip is capable of concealing or masking the most extreme bitter taste when the active therapeutic agent is adsorbed on magnesium aluminum silicate and is appropriately selected from the group consisting of amines and fatty acid-amine salts.

Preferably the magnesium aluminum silicate is micronized and finer than 325 mesh. The active therapeutic agent adsorbed on the magnesium aluminum silicate is, depending upon the particular agent, an amine or a fatty acid-amine salt. The fatty acid of the fatty acid amine salt may be a saturated fatty acid such as stearic acid or an unsaturated fatty acid such as oleic acid.

The foam, as delivered from an aerosol canister, has the consistency of whipped cream, is stable for extended periods and is hostile to the growth of microorganisms so that refrigeration is not required. It can be safely ingested so that it is ideal as a carrier for active agents, especially oily or oil-soluble medicines, vitamins, minerals or other therapeutic agents. Because the foam of this invention masks the taste of bitter amine drugs, such as phenylpropanolamine base, dyclonine base, steroids, etc., it makes it easier to administer large amounts of high dosage medications, so that greater effectiveness and compliance can be achieved than is common with conventional therapeutic forms. Similar desirable results can be achieved with antitussives such as dextromethorphan base, antihistamines such as chlorpheniramine base, decongestants such as pseudoephedrine base and local anesthetics such as benzocaine or dyclonine base.

The stability of the novel foam formulation enables it to be controlled in the sense that it can be measured on a spoon or a similar device for oral administration, or measured into an applicator for rectal or vaginal administration. Obviously, such a foam is capable of being packaged in small, portable aerosol containers (the size of a typical breath spray container) which may be easily transported in a pocket or purse as well as in shaving cream-sized containers for home use.

While not wishing to be limited to any particular theory, it is believed that the formulations of the present invention are capable of achieving the foregoing results without valve clogging due to a novel combination of ingredients that produces a high viscosity formulation capable of keeping the small solids particles dispersed and of lubricating the aerosol valve.

In a preferred embodiment of the present invention, the propellant comprises 1 to 10 wt. of the composition, the foaming agent comprises 2 to 40 wt. the solid particles comprise at least 15 wt. and are insoluble in the other ingredients of the composition, and the balance of the composition is the liquid oil.

The liquid oil may be a non-therapeutic agent selected from the group consisting cf soybean oil, partially hydrogenated soybean oil, linseed oil, corn oil, peanut oil, sunflower oil, cottonseed oil, olive oil, liquid petrolatums, oleic acid, lauric acid and mono- and diglyceride oils, or it may be an active therapeutic agent selected from the group consisting of mineral oil, castor oil, fish liver oils, fish body oils, and various oil-soluble ingredients.

Typically the propellant is a hydrocarbon, preferably propane. The foaming agent is selected from the group consisting of lecithin, polyglycerol esters of fatty acids having an HLB (hydrophilic/lipophilic balance) value of between 4.0 and 13.0, glycerol esters of fatty acids having an HLB value of between 2.5 and 4.5, sorbitan esters of fatty acids having an HLB value of between 3.0 and 7.0 and mixtures thereof. The solid particles may also include ingredients selected from the group consisting of powdered skim milk, powdered flavors, sugars, and sugarless sweeteners, with powdered sugar being a preferred solid particle. The solid particles are insoluble in the other ingredients of the foam composition and have an average size in the range of 50 to 100 microns.

The present invention also encompasses, as an article of manufacture, a pressurized aerosol container, the container having therein an edible, anhydrous aerosol foam composition. The composition comprises a foamable liquid oil, a foaming agent and a propellant, the propellant being present in an amount sufficient to produce a stable, measurable foam but insufficient to produce a spray when the composition is ejected through an aerosol valve, and at least 15% by weight of dispersed solid particles including an active therapeutic agent adsorbed on magnesium aluminum silicate. The active therapeutic agent is selected from the group consisting of amines and fatty acid-amine salts.

The present invention further encompasses methods of manufacturing the edible, anhydrous aerosol foam compositions. Where the active therapeutic agent adsorbed on the magnesium aluminum silicate is an amine, the method comprises the steps of agitating a mixture of a foamable liquid oil, a foaming agent, a bitter active therapeutic agent in amine base form (whether as dissolved solid particles or a liquid), and dispersed solid particles of magnesium aluminum silicate, to form in situ a non-bitter adsorbate of the amine therapeutic agent on the silicate. An aerosol can is filled with the oil, the foaming agent, the adsorbate, and propellant in an amount sufficient to produce stable, measurable foam but insufficient to produce a spray when the composition is ejected through an aerosol valve, the composition containing at least 15% by weight of dispensed solid particles.

Where the active therapeutic agent adsorbed on magnesium aluminum silicate is a fatty acid-amine salt, the initial step comprises heating a mixture of the foamable liquid oil, the foaming agent, the bitter active therapeutic agent in amine base form, and an oil-soluble fatty acid to form the fatty acid-amine salt. Next, the mixture is agitated with dispersed solid particles of magnesium aluminum silicate, to form in situ a non-bitter adsorbate of the fatty acid-amine salt of the therapeutic agent on the silicate. Finally, the aerosol can is filled, as before.

DETAILED DESCRIPTION OF THE PREFERRED EMBODIMENTS

The essential components of the present invention are:
1. A foamable, edible, anhydrous liquid oil.
2. A foaming agent (surfactant system).
3. At least a 15% concentration by weight of dispersed solids including an adsorbate of an active therapeutic agent on magnesium aluminum silicate
4. A food grade propellant.

THE LIQUID OIL

The liquid oil can be inert, an active therapeutic agent of the system (as in the case of fish oil or mineral oil), or the carrier for an oil-soluble active agent (as in the case of oil-soluble therapeutic agents, e.g., oil-soluble vitamins). As used throughout the specification, the term "oils" includes "oil-soluble active agents".

The foamable, edible anhydrous liquid oils utilized in the present invention are varied and of no great critical significance except where they are themselves active agents. Typical among the edible organic oils useful for the present invention are those such as soybean oil, partially hydrogenated soybean oil, vegetable oil, linseed oil, corn oil, peanut oil, sunflower oil, cottonseed oil, olive oil, liquid petrolatum, oleic acid, lauric acid, and mono-and diglyceride oils. As indicated above, the basic criteria for a liquid oil utilizable in the present invention are that it is foamable and edible.

Typically, the edible oils utilized in the present invention are present in the formulation in a percentage of 35 to 75% by weight of the total composition. A preferred range is 45 to 70% by weight of the total composition. The amount of oil may be varied based upon the nature and amount of the other ingredients in the formulation, such as the amount of dispersed solids. Ordinarily, the percentage amount of each other ingredient in the formulation is first selected, and the oil is the ingredient added to bring the formulation to 100%.

The present invention provides a valuable delivery system for the oral administration of oily medicinal agents such as the following: mineral oil as a lubricant laxative, castor oil as an irritant laxative, cod liver and other fish liver oils as natural sources of vitamins A and D, fish body oils containing Omega 3 fatty acids as blood cholesterol reducers for the prevention of heart attacks, oil-soluble vitamins (such as vitamins A, D, E, and K), oil-soluble therapeutic agents (such as steroid hormones, e.g. estradiol, testosterone, progesterone, cortisone and hydrocortisone), sympathomimetics (such as epinephrine, isoproterenol, phenylpropanolamine, ephedrine, and amphetamine), anesthetics (such as dibucaine, dyclonine, and lidocaine), sedatives (such as diphenhydramine and chloral hydrate), parasiticides (such as benzyl benzoate), and other oil-soluble medicinal agents. The active pharmaceutical materials in oil form which can be incorporated in the foam of the present invention can be any of the common analgesics, antitussives, laxatives, vitamins, minerals, or any other type of therapeutic agent. Indeed, therapeutic agents which are normally in a water-soluble solid particle form (e.g., dyclonine HCl, phenylpropanolamine HCl) can be converted to oil-soluble amine bases and initially incorporated as such in the oil of the present invention. Certain therapeutic liquid amine bases such as diphenhydramine and dyclonine can be dissolved directly in the oil of the present invention.

This novel system permits the preparation of unique products that solve the significant problem of the stability of oils (or oil-soluble active agents) that are vulnerable to oxidation. Since oxygen can easily be excluded from the system in the aerosol can, the integrity of oils such as fish oil containing Omega 3 fatty acids can be preserved. Similarly, cod liver oil and other fish liver oils can be maintained for long periods of time without loss in vitamin potency or oxidation of their unsaturated fatty acids. Oil-soluble vitamins can be dissolved in the oils in these systems and their potency can be maintained over the shelf life of such products.

THE FOAMING AGENT

Foaming agents utilizable in the present invention are selected from the group consisting of lecithin and various polyol fatty acid esters and mixtures thereof. Lecithin is the commercial name for a class of naturally occurring compounds derived from soybeans. These compounds are phosphatides and phospholipids. The principal components of lecithin are a naturally occurring mixture of phosphatidyl choline, phosphatidyl ethanolamine, inositol phosphatides and related phosphorous containing lipids. Chemically, lecithin is described as phosphatidyl choline and is a mixture of the diglycerides of stearic, palmitic and oleic acids linked to the choline ester of phosphoric acid. It is available commercially as a 60% solution in soybean oil or as a granular powder essentially free of soybean oil. A hydroxylated lecithin, modified to increase the hydrophilic properties is also commercially available. This hydroxylated lecithin is commonly supplied as a 60% solution in soybean oil.

The polyol fatty acid esters utilizable in the present invention are commercial products and are comprised of three types:
1. Glycerol esters of fatty acids.
2. Polyglycerol esters of fatty acids.
3. Sorbitan esters of fatty acids.

The glycerol esters which have been found to be advantageous in generating a suitable anhydrous edible aerosol foam are prepared by standard esterification methods and have an HLB of between 2.5 and 4.5. Among the preferable glycerol fatty esters utilizable in the present invention are those such as glycerol monostearate (HLB 3.2) and glycerol monooleate (HLB 3.4).

The polyglycerol esters utilizable in the present invention are commercial products prepared by first polymerizing glycerine under alkaline conditions. The polymerization is controlled to yield the particular desired average molecular weight. Investigations indicate that the Polymerization of glycerol Progresses predominately in a straight-chain manner. The esters are prepared by reacting the Polyglycerol with a specific fatty acid or by the alcoholysis of a triglyceride. by this method, it is possible to prepare esters ranging anywhere from hydrophilic monoesters such as decaglycerol monolaurate to a lipophilic decaglycerol decaoleate.

The polyglycerol esters preferably used in the present invention have an HLB value of between 4.0 and 13.0. These have been found to be most advantageous in generating a suitable anhydrous aerosol foam. Among the preferable polyglycerol esters utilizable in the present invention are those such as: hexaglycerol distearate (HLB 4.0), decaglycerol tetraoleate (HLB 6.0), triglycerol monostearate (HLB 7.0), triglycerol monooleate (HLB 7.0), octaglycerol monostearate (HLB 12.0) and octaglycerol monooleate (HLB 13.0).

The sorbitan fatty acid esters which have been found to be advantageous in generating a suitable anhydrous edible aerosol foam are commercial products prepared by standard esterification methods and have an HLB of between 3.0 and 7.0. Among the preferable sorbitan esters utilizable in the present invention are those such as sorbitan monostearate (HLB 4.7), sorbitan monooleate (HLB 4.3), and sorbitan monopalmitate (HLB 6.7).

Additionally, a combination of any of the polyol fatty acid esters may be utilized in the present invention.

The polyol fatty acid esters are somewhat more hydrophilic than lecithin so that their use allows the foamable, edible anhydrous liquid oil to be more easily dispersed when contacted with an aqueous medium. This gives a much less oily feel in the mouth and releases the suspended medicament more rapidly in the stomach. Additionally, they may be used in conjunction with lecithin in the same system which causes the lecithin to become more hydrophilic and therefore more palatable than the lecithin alone. This combination also causes the release of an active agent—whether oil or solid—faster in the stomach. As it is necessary for the final product to be edible, the polyol esters are approved for internal use by the Food and Drug Administration.

The foaming agent utilized in the present invention is present in an amount of from 2 to 40% by weight. The amount of foaming agent utilized depends upon the particular foaming agent being utilized, the particular foamable, edible, anhydrous liquid oil being utilized and the propellant system. A preferred range of foaming agent is from about 3 to 15% by weight of the composition, with 10% being especially preferred. It is a particularly desirable additional feature of the foaming agents that they possess surfactant properties and, therefore, affect the rate at which the active ingredient of the foam—whether oil or dispersed solid—is released in the mouth. Accordingly, some variations in the amount of foaming agent in a particular formulation may be purposely chosen based on the nature of the active ingredient in order to control the rate of release.

THE PROPELLANT

The edible propellant can be selected from the class of hydrocarbons that are gaseous under atmospheric pressures and liquefy when compressed, or certain edible fluorocarbons such as FREON 115. The most commonly used are propane, butane and isobutane. Propane is approved for use in ingested products and can be obtained commercially in an odorless and tasteless form which is ideally suited for use in preparing the whip of the present invention. Since these liquefied gases are soluble in the oil vehicle of the composition, there is a resulting reduction in their vapor pressure. Therefore, it is most advantageous to use propane since it has the highest pressure of the three generally available hydrocarbon propellants and, even when dissolved in the low concentrations normally employed in this invention, produces a product with a pressure of 30–40 pounds per square inch over atmospheric pressure. This pressure is required to eject the foam from the container and produce a stable, dense foam which can be measured onto a spoon to facilitate administration. However, since propane is soluble in the oil base, there is very little pressure drop from the first to the last actuation of the aerosol valve and a satisfactory foam is produced when each dose is expelled.

The amount of propellant used is critical since too much will produce an undesirable spray rather than the desired stable, measurable foam. Amounts of propellant in the range of from 1–10 wt. % are operative, but 3–5 wt. % is the preferred concentration based upon the total weight of the contents of the aerosol container. The amount of propellant used may vary somewhat, depending upon the nature and amount of the other ingredients in the composition but, in all cases, the lowest amount sufficient to form a stable, measurable foam without forming an unmeasurable spray will be selected.

Propellants other than the liquefied hydrocarbon and fluorocarbon gases can be used, including edible compressed gases like nitrogen, nitrous oxide and carbon dioxide, although they do not produce the most desirable foams over the life of the product in use.

THE DISPERSED SOLIDS

A particularly important and surprising feature of the foams of this invention is their ability to suspend high concentrations, i.e., up to 50% by weight, of solids, and mask their taste upon ingestion of the foam. Preferably, the suspended particles are ground to a very fine particle size since this facilitates the formation and maintenance of a uniform dispersion and prevents clogging. Particle sizes in the range of 50 to 100 microns in diameter are preferred.

The foam of the present invention will contain at least 15 wt. % of suspended solid particles and can contain up to 50 wt. of suspended solid particles without any appreciable valve malfunctioning. This ability to suspend high percentages of solids without valve malfunctioning enables the aerosol foam system of the present invention to be utilized for a wide variety of formulations. The reasons for the unique ability of the foams to suspend such a high concentration of solids without valve clogging are not fully understood, but it is believed to result from a combination of the small particle size, the high viscosity of the foam formulation due to its low propellant content which aids in keeping the particles dispersed and reduces agglomeration and settling, and the lubricating effect of the oil on the valve.

These suspended solid particles serve to modify the taste characteristics of the oil to make it less greasy and also serve to make the foam more dense by their physical presence adding substance to the foam. They also serve as foci for evaporation of the propellant when exposed to the atmosphere upon expulsion from the aerosol can. This makes the foam more dense and physically stable in much the same way as meringues are made stable by beating air into egg whites or whipped cream is made stable by beating air into cream.

Medicaments that normally require refrigeration to prevent dry out or spoilage due to air oxidation, can be prepared in this system with extended shelf life, requiring no refrigeration or protection from the atmosphere.

Powdered sugar is one of the preferred dispersed solids since it provides good taste and mouth feel characteristics to the foam, in addition to providing the beneficial physical effects described above. Sugars other than sucrose (such as fructose) or "sugarless" sweeteeners (such as mannitol, saccharine, aspartame, glycyrrhizins and sorbitol) can be employed. Other dispersed solids can also be used such as powdered skim milk, lakes of colors (i.e., pigments), powdered flavors, etc., depending upon the needs of the specific product formulation. In all cases the particle size should be less than 100 microns to prevent clogging the valves of the aerosol.

The dispersed solids may be an exothermic agent such as anhydrous sodium aluminosilicate (commercially available under the name Valfor 950). Upon exposure to water the exothermic agent undergoes a heat-producing reaction capable of warming up the dispensed foam. A foam containing such an exothermic agent may find utility in a therapeutic setting where the heat may enhance the absorption of therapeutic agents in the foam by the body. While the useful exothermic agents are not particularly pleasant tasting, the composition can be given an acceptable taste through the use of sugars, flavorings, and the like as taught herein.

Regardless of whether or not the liquid oil is or contains an active therapeutic agent, the dispersed solids of the present invention always contain one or more active therapeutic agents adsorbed on magnesium aluminum silicate. The magnesium aluminum silicate adsorbent complexes the active therapeutic agent on its surface and prevents it from contacting the taste buds of the mouth. The adsorbent is especially useful in conjunction with other dispersed solids, such as sugars, which mask any residual tastes of the distasteful ingredients.

The magnesium aluminum silicate is preferably in a micronized or microfine powder form available under the trade name Veegum F from R. T. Vanderbilt Company, Inc. of Norwalk, Ct. The micronized product is finer than 325 mesh with a maximum size of 45 microns. For reasons which are not fully understood, as illustrated in Example 8, other adsorbents, even other clay adsorbents, do not function qualitatively as well as the magnesium aluminum silicate in masking bitterness.

The active therapeutic agent adsorbed on the magnesium aluminum silicate is selected from the group consisting of amines and fatty acid-amine salts. The agent is preferably a fatty acid-amine salt as all such oil-soluble salts can have their bitter nature masked or deactivated by the adsorbent. The fatty acid-amine salt is formed by reacting the amine form of the active therapeutic agent with a fatty acid.

The fatty acid may be saturated, such as stearic acid (preferably triple pressed stearic acid which contains a fraction of palmitic acid), or unsaturated, such as oleic acid. Lower carbon fatty acids tend to have an undesirable taste themselves, and thus the higher carbon fatty acids are preferred, such as those having 16 or more carbon atoms. As evidenced by Example 7, acids other than fatty acids are not operable in the present invention.

The fatty acid is used at least slightly in excess of the stoichiometric amount required to ensure complete reaction of the amine, although excessive fatty acid should be avoided where the fatty acid itself is not particularly palatable. Sufficient time is preferably provided for completion of the amine/fatty acid reaction before introduction of the magnesium aluminum silicate to the mixture. To ensure full solvation of the fatty acid and a reasonable reaction time, the reaction mixture is heated, preferably to about 60°-70° C. with stirring. The resultant fatty acid-amine salt is itself oil-soluble.

In the case of certain active therapeutic agents, however, it has been found that the active therapeutic agent adsorbed on the magnesium aluminum silicate may be an amine rather than a salt. It is not understood why, or predictable when, an effective taste-neutralizing adsorbate may be formed using the amine form of one active therapeutic agent, while in the case of another active therapeutic agent an effective adsorbate is formed only by using the fatty acid-amine salt form of the active therapeutic agent. As evidenced by Example 3, the fatty acid-amine salt is itself typically as bitter as the amine base itself. However, for any given active therapeutic agent, it is a simple, rapid and inexpensive matter to determine initially whether an effective adsorbate may be formed using the amine base. If not, then one simply resorts to the fatty acid-amine salt. If desired, one may always employ the fatty acid-amine salt, but this may result in an unnecessary use of the fatty acid ingredient, and hence increased material and processing costs. Among the amine active therapeutic agents requiring salt formation are dextromethorphan, pseudoephedrine, diethyl carbamazine and phenylpropanolamine. Among the amine active therapeutic agents not requiring salt formation are trimethoprim (a urinary tract drug) and many vitamins (such as $B_1$, $B_2$, $B_6$ and niacinamide).

The amount of magnesium aluminum silicate used to form the adsorbate should be at least equal to the amount of the amine or salt to be adsorbed thereon and is preferably many times greater than that—for example, 5–10 times greater on a weight basis.

Because the adsorbent is believed to operate by complexing, adsorbing, or otherwise isolating the drug from the taste buds, the strength with which it can maintain the drug isolated should determine its effectiveness. It is unclear, however, whether the failure of the adsorbate to neutralize the bitter taste of a drug reflects the failure of the adsorbent to isolate or trap the drug, on the one hand, or its failure in some other respect to neutralize the bitterness even though an adsorbate is formed, on the other hand. In any case, the adsorbates of the present invention have utility in masking or overcoming primarily the bitter taste of the adsorbed drug as opposed to its saltiness or other undesirable taste. Accordingly, references herein to the efficacy of the adsorbate in overcoming the unpalatable taste of the amine or salt should be understood as references to overcoming the bitterness thereof.

In preparing the aerosol foam composition where the therapeutic agent will be adsorbed in amine form, the foamable liquid oil, the foaming agents or surfactants, dissolved solid particles or a liquid of the bitter active therapeutic agent in amine base form, and any other oil-soluble ingredients, are heated together to about 60° C. Then the magnesium aluminum silicate and any other solids are added to the oil phase with agitation, preferably for about 5–15 minutes, to form in situ a non-bitter adsorbate of the amine therapeutic agent on the clay. After further cooling to 40° C., flavors are added and the composition is mixed well. The composition is then passed through a homogenizer or colloid mill to disperse agglomerates. An aerosol can is filled with the composition, and an aerosol valve is then crimped on. Finally, food grade propellant is added through the valve, and the can shaken well to dissolve the propellant in the system.

The method of preparing the aerosol foam composition where the therapeutic agent will be adsorbed in fatty acid-amine salt form is generally similar except for initially heating a mixture of the foamable liquid oil, the foaming agents or surfactants, an oil-soluble fatty acid, and dissolved solid particles or a liquid of a bitter active therapeutic agent in amine base form to form the oil-soluble fatty acid-amine salt. This heated mixture is then agitated with dispersed solid particles of the magnesium aluminum silicate to form in situ a non-bitter adsorbate of the fatty acid-amine salt of the therapeutic agent on the clay. Finally, the composition is cooled and treated as indicated above.

GENERAL

The oily or greasy mouthfeel of the oils can be minimized and largely eliminated, so that the final taste of the product can be very pleasant, by the three other essential components of this unique system. The first method of reducing oiliness in the mouth is provided by the high concentrations of dispersed solids which the system of this invention can tolerate, and indeed requires. This effect is analogous to the taste difference that exists between shortening which is greasy and cake icing which is pleasant. The difference is that, in the case of icing, the shortening is mixed with large amounts of powdered sugar so that, when ingested, the sugar dissolves in the mouth and dilutes the greasy effect of the shortening. In the system of this invention large concentrations of sugar can be mixed with the oils to provide the same effect in the mouth.

The second method of reducing oiliness in the mouth is provided by the foaming agent, which is one or more edible surfactants. Since these surfactants modify the oils to make them more water-dispersible, it has been found that the system becomes more dispersible in the aqueous fluids in the mouth and this further reduces the greasy mouthfeel the oils normally possess. And since we have found that it is possible to adjust this effect by increasing the water-dispersibility of the surfactant system, an even greater reduction in greasiness in the mouth can be effected.

The third method of reducing oiliness in the mouth is provided by the edible propellant, which is an essential component of the system. Since the propellant causes the composition to expand and foam when it is expelled from the aerosol can, the density of the product is greatly reduced. In fact the density changes from about 1.0 g/cc in the can to about 0.25 g/cc when the foam is formed upon expulsion from the can. This fourfold reduction in density (or increase in volume for a given weight of product) provides a further dilution of the oil in the product so that greasiness is even further reduced upon ingestion.

Thus the system provides three ways to reduce oiliness or greasiness of oils upon ingestion—dispersed solids to overcome the flavor of the oily taste, surfactants to disperse the oil in the mouth, and propellant to reduce the density of the oil.

Since the system of this invention is completely anhydrous, it provides a very poor medium for the growth of microorganisms. And if sugar is used as one or all of the dispersed solids, it has been found that the system is actively bactericidal. This surprising effect was discovered when formulations of this invention were deliberately inoculated with aqueous suspensions of microorganisms. It was expected that these organisms would not grow in the medium of the product. But it was found that the organisms were killed in the product, even though no chemical preservative was present. This effect was found with all the organisms used, even pathogenic anaerobes like Clostridium which could be expected to remain viable in systems where air was excluded. The system of this invention was found to be cidal to these organisms so that within a week the number of organisms present was reduced to substantially zero. This cidal effect means that contamination by microorganisms during the manufacture of this product is unlikely. In addition, the product that remains in the spout of the aerosol can during use by the consumer will not be contaminated by organisms from the environment.

In addition to the essential ingredients of the foam, there may also be incorporated in the foams of the present invention any of a variety of additives or a combination thereof, commonly added to aerosol compositions or to toiletries, cosmetics, or pharmaceuticals. Typically, such additives are those such as emollients, lubricants, humectants, abrasives, and perfumes. Thus, the edible anhydrous aerosol foam of the present invention may be used as a vehicle for any of a large variety of active pharmaceutical materials or cosmetic ingredients. Additionally, the foam itself can be used as a base for various sweetening and flavoring agents in order to simulate a food item.

EXAMPLES

All parts are by weight, unless otherwise indicated.

Examples 1 through 8 illustrate the simple short test procedures used to determine whether a non-bitter adsorbate is obtained. Examples 1 and 2 illustrate the failure to obtain a non-bitter adsorbate simply by substituting oil for water in the standard aqueous procedure for forming an adsorbate, regardless of whether one utilizes a halide salt or amine form of the active therapeutic agent. Example 3 illustrates that the mere transformation of an amine form of the active therapeutic agent into the fatty acid-amine salt does not alter the bitterness of the drug. Examples 4 and 5 illustrate the formation of non-bitter fatty acid-amine adsorbates using stearic and oleic acids, respectively, as the fatty acid. Example 6 illustrates the formation of non-bitter fatty acid-amine adsorbates using a variety of different bases. Example 7 illustrates that a non-fatty acid-amine salt does not result in a non-bitter adsorbate formation. Example 8 illustrates that other adsorbents cannot be substituted for magnesium aluminum silicate. Thus Examples 1–3 and 7–8 represent controls in which a non-bitter adsorbate was not obtained.

Examples 9–11 illustrate edible whips or foams according to the present invention. Examples 9 and 10 use fatty acid-amine adsorbates, while Example 11 uses an amine adsorbate.

Unless otherwise indicated, each formulation of Examples 9–12 was prepared according to the following general instructions: Heat the oils, the surfactants, and any other oil-soluble ingredients together to 60° C.±5° C. Then add the solids to the oil phase with vigorous agitation to assure uniform dispersion (5–15 minutes). After cooling to 40°±5° C., add any flavors and mix well. Pass the composition through a homogenizer or colloid mill to disperse agglomerates. Fill an aerosol can with the composition and then crimp on an aerosol valve. Add the propellant through the valve. Shake well to dissolve the propellant in the system.

EXAMPLE 1

(Control)

5.0 gm. of Veegum F, a micronized form of magnesium aluminum silicate, was heated in 94.5 gm. of partially hydrogenated soybean oil at a temperature of 60° C.; 0.5 gm. of dextromethorphan HBr was added with agitation. Upon cooling, the batch was tasted. The extremely bitter taste of the dextromethorphan was still evident.

EXAMPLE 2

(Control)

Example 1 was repeated substituting dextromethorphan base for Dextromethorphan HBr. The batch when cooled was tested. The bitterness of the dextromethorphan was still evident.

EXAMPLE 3

(Control)

0.5 gm. of dextromethorphan base was dissolved in 92.5 gm. of partially hydrogenated soybean oil heated to 60° C.; 2.0 gm. of stearic acid T.P. was then added and dissolved. The batch was cooled and tasted. The dextromethorphan-stearic acid salt was still very bitter.

EXAMPLE 4

Example 3 was repeated with 5.0 gm. of Veegum F being added to the heated batch. The batch was cooled and tasted. No bitter taste was evident.

EXAMPLE 5

Example 4 was repeated with oleic acid substituted for the stearic acid. The same loss of bitterness was evident.

EXAMPLE 6

Example 4 was repeated four times using in turn pseudoephedrine base, phenolpropanolamine base, an equal mixture of the two bases and diethyl carbamazine base (a drug used in dog heartworm therapy) in lieu of dextromethorphan base. Each drug lost its bitterness by this method.

EXAMPLE 7

(Control)

The portion of Example 6 using diethyl carbamazine base was repeated using diethyl carbamazine citrate salt in lieu of the diethyl carbamazine stearate salt. The drug retained an extremely bitter taste.

EXAMPLE 8

(Control)

Example 4 was repeated eight times, using in turn (in lieu of magnesium aluminum silicate) 5.0 gm of one of the following adsorbents:
Activated attapulgate (Pharmasorb)
Hydrated Aluminum Silicate (Bentonite, N.F.)
Magnesium Trisilicate U.S.P.
Hydrous Magnesium Silicate U.S.P. (Talc)
Synthetic Calcium Silicate (Microcel)
Silicon Dioxide (Diatomaceous Earth)
Colloidal Silicon Dioxide (Cab-O-Sil)
Fumed Silicon Dioxide In each instance, the bitter taste of the dextromethorphan was evident.

EXAMPLE 9

Antitissusive, Decongestant Edible Whip

|  | % |
| --- | --- |
| Dextromethorphan Base (amine drug) | 0.37 |
| Phenylpropanolamine Base (amine drug) | 0.50 |
| Magnesium Aluminum Silicate (clay) | 15.00 |
| Stearic Acid (fatty acid) | 3.00 |
| Sorbitan Monostearate (foaming agent) | 2.00 |
| Hexaglycerol Dioleate (foaming agent) | 8.00 |
| Sugar 12X (sweetener) | 14.00 |
| Colloidal Silicon Dioxide (anti-caking agent) | 1.00 |
| FM Cherry Flavor 23501 (flavor) | 0.40 |
| FD & C Red 640 in HVO (colorant) | 0.20 |
| Aspartame (sweetener) | 0.15 |
| Citric Acid, anhydrous (acidifier) | 0.50 |
| Soybean oil, partially hydrogenated (oil) | 50.88 |
| Propane (propellant) | 4.00 |
|  | 100.00% |

The two bases were dissolved in a mixture of the soybean oil, the foaming agents (sorbitan monostearate and hexaglycerol dioleate) and the stearic acid, at 70° with stirring. The red colorant was added with mixing.

The clay was added and the suspension stirred for an additional 5 minutes. Then the sugar, the colloidal silicon dioxide, and the anhydrous citric acid were added, and the mixture stirred until the solids were completely dispersed. The mixture was next cooled to 40° C. and the cherry flavor and aspartame added with mixing. After the mixture was well mixed, aerosol cans were filled with the mixture and pressurized with the propane.

Each 2 gram spoonful provides 10 mg. dextromethorphan hydrobromide equivalent and 12.5 mg. phenylpropanolamine hydrochloride equivalent. No bitter taste was evident.

EXAMPLE 10

Decongestant Edible Whip

|  | % |
| --- | --- |
| Pseudoephedrine Base | 0.82 |
| Magnesium Aluminum Silicate | 11.00 |
| Stearic Acid | 2.00 |
| Colloidal Silicon Dioxide | 2.00 |
| Hexaglycerol Dioleate | 8.00 |
| Sorbitan Monostearate | 2.00 |
| Sugar 12X | 10.00 |
| Aspartame | 0.20 |
| FD & C Red 40 Lake in oil | 0.20 |
| FM Cherry Flavor 28858-63 | 0.40 |
| Citric Acid, anhydrous powder | 0.30 |
| Soybean oil, partially hydrogenated | 60.08 |
| Propane | 3.00 |
|  | 100.00% |

The procedure of Example 9 was followed.
Each three gram spoonful provides 30 mg. of pseudoephedrine HCl equivalent. No bitter taste was evident.

EXAMPLE 11

Trimethorprim Edible Whip

|  | % |
| --- | --- |
| Trimethoprim | 1.30 |
| Veegum F (Magnesium Aluminum Silicate) | 3.00 |
| Lecithin, granular | 4.00 |
| Sorbitan Monostearate | 4.00 |
| Cabosil M-5 | 1.00 |
| Sugar, powdered, 12x, NF | 25.00 |
| Flavor | 0.20 |
| Soybean Oil, partially hydrogenated | 57.50 |
| Propane | 3.00 |
|  | 100.00% |

The lecithin, sorbitan monostearate and soybean oil were heated to 60° C. The trimethoprim and Veegum F were stirred in well. After cooling the mixture to 50° C., the Cabosil M-5 and the sugar were added. After continued cooling, flavor was added. The mixture was milled and submitted for aerosol filling.

Each teaspoon (3.0 g.) delivered 40 mg. of trimethoprim. No bitter taste was evident.

To summarize, the present invention provides a stable, edible anhydrous aerosol foam or whip which can mask the bitter taste of an amine active therapeutic agent, even at a high therapeutic concentration. The foam employs an adsorbate formed in situ, without requiring any pre-formation of the adsorbate, so that the foam may be easily and rapidly formed.

Now that the preferred embodiments of the present invention have been described in detail, various modifications and improvements thereon will become readily apparent to those skilled in the art. Accordingly, the present invention is to be construed broadly and in a manner consistent with the spirit and scope of the invention herein.

We claim:

1. An edible, anhydrous aerosol foam composition comprising a foamable liquid oil, a foaming agent, a propellant, and dispersed solid particles, said propellant being present in an amount sufficient to produce a stable, measurable foam but insufficient to produce a spray when said composition is ejected through an aerosol valve, and said dispersed solid particles being at least 15% by weight of said composition and including an active therapeutic agent adsorbed on magnesium aluminum silicate, said active therapeutic agent being selected from the group consisting of amines and fatty acid-amine salts.

2. The composition of claim 1 wherein said active therapeutic agent is an amine.

3. The composition of claim 1 wherein said active therapeutic agent is a fatty acid-amine salt.

4. The composition of claim 1 wherein said magnesium aluminum silicate is micronized and finer than 325 mesh.

5. The composition of claim 1 wherein said fatty acid is a saturated fatty acid.

6. The composition of claim 1 wherein said fatty acid is stearic acid.

7. The composition of claim 1 wherein said fatty acid is an unsaturated fatty acid.

8. The composition of claim 1 wherein said fatty acid is oleic acid.

9. The composition of claim 1 wherein said propellant comprises 1 to 10 wt. % of said composition.

10. The composition of claim 1 wherein said propellant is a hydrocarbon.

11. The composition of claim 1 wherein said propellant is propane.

12. The composition of claim 1 wherein said solid particles are insoluble in the other ingredients of said foam composition.

13. The composition of claim 1 wherein the average size of said solid particles is in the range of 50 to 100 microns.

14. The composition of claim 1 wherein said solid particles are selected from the group consisting of powdered skim milk, crushed nut solids, powdered flavors, sugars, sugarless sweeteners, and clays.

15. The composition of claim 1 wherein said solid particles comprise powdered sugar.

16. The composition of claim 1 wherein said foaming agent is selected from the group consisting of lecithin, polyglycerol esters of fatty acids having an HLB value of between 4.0 and 13.0, glycerol esters of fatty acids having an HLB value of between 2.5 and 4.5, sorbitan esters of fatty acids having an HLB value of between 3.0 and 7.0 and mixtures thereof.

17. The composition of claim 1 wherein said foaming agent comprises 2 to 40 wt. % of said composition.

18. The composition of claim 1 wherein said foaming agent is substantially comprised of at least one water-dispersible surfactant.

19. The composition of claim 1 wherein said liquid oil is selected from the group consisting of soybean oil, partially hydrogenated soybean oil, linseed oil, corn oil, peanut oil, sunflower oil, cotton seed oil, olive oil, liquid petroleums, oleic acid, lauric acid and mono- and diglyceride oils.

20. The composition of claim 1 wherein said propellant comprises 1 to 10 wt. % of said composition, said foaming agent comprises 2 to 40 wt. % of said composition, said solid particles comprise at least 15 wt. % of said composition and are insoluble in the other ingredients of said foam composition, and the balance of said composition is said liquid oil 21. As an article of manufacture, a pressurized aerosol container, said container having therein an edible, anhydrous aerosol foam composition comprising a foamabale liquid oil, a foaming agent, a propellant, said propellant being present in an amount sufficient to produce a stable, measurable foam but insufficient to produce a spray when said composition is ejected through an aerosol valve, and at least 15% by weight of dispersed solid particles including an active therapeutic agent adsorbed on magnesium aluminum silicate, said active therapeutic agent being selected from the group consisting of amines and fatty acid-amine salts.

22. The container of claim 21 wherein said active therapeutic agent is an amine.

23. The container of claim 21 wherein said active therapeutic agent is a fatty acid-amine salt.

* * * * *